(12) United States Patent
Healy et al.

(10) Patent No.: US 6,607,553 B1
(45) Date of Patent: Aug. 19, 2003

(54) METHOD FOR DEPLOYING A THERMO-MECHANICALLY EXPANDABLE STENT

(75) Inventors: Kevin E. Healy, Moraga, CA (US); Joseph T. Walsh, Evanston, IL (US); Gary S. Dorfman, Saunderstown, RI (US)

(73) Assignee: B. Braun Medical, Inc., Bethlehem, PA (US)

( * ) Notice: Subject to any disclaimer, the term of this patent is extended or adjusted under 35 U.S.C. 154(b) by 111 days.

(21) Appl. No.: 09/715,215

(22) Filed: Nov. 17, 2000

(51) Int. Cl.$^7$ .................................. A61F 2/06
(52) U.S. Cl. ............... 623/1.11; 623/1.19; 623/1.21; 623/1.46
(58) Field of Search ................. 623/1.11, 1.19, 623/1.21, 1.46; 427/2.25; 424/426

(56) References Cited

U.S. PATENT DOCUMENTS

| | | | |
|---|---|---|---|
| 4,733,665 A | 3/1988 | Palmaz | 128/343 |
| 4,776,337 A | 10/1988 | Palmaz | 128/343 |
| 4,920,203 A | 4/1990 | Tang et al. | 525/409 |
| 5,147,385 A | 9/1992 | Beck et al. | 623/1 |
| 5,226,430 A | 7/1993 | Spears et al. | |
| 5,292,321 A | 3/1994 | Lee | 606/28 |
| 5,443,458 A | 8/1995 | Eury | 604/891.1 |
| 5,531,716 A | 7/1996 | Luzio et al. | 604/265 |
| 5,562,653 A | 10/1996 | Thompson | 604/890.1 |
| 5,612,050 A | 3/1997 | Rowe et al. | 424/423 |
| 5,634,946 A | 6/1997 | Slepian | 623/11 |
| 5,662,712 A | 9/1997 | Pathak et al. | 623/12 |
| 5,665,063 A | 9/1997 | Roth et al. | 604/53 |
| 5,670,161 A * | 9/1997 | Healy et al. | 424/426 |
| 5,698,189 A | 12/1997 | Rowe et al. | 424/78.08 |
| 5,741,323 A | 4/1998 | Pathak et al. | 623/1 |
| 5,749,915 A | 5/1998 | Slepian | 623/1 |
| 5,749,922 A | 5/1998 | Slepian et al. | 623/1 |
| 5,776,184 A | 7/1998 | Tuch | 623/1 |
| 5,788,979 A | 8/1998 | Alt et al. | 424/426 |
| 5,844,016 A | 12/1998 | Sawhney et al. | 522/13 |
| 5,849,035 A | 12/1998 | Pathak et al. | 623/1 |
| 5,947,977 A * | 9/1999 | Slepian et al. | 606/108 |
| 5,989,244 A * | 11/1999 | Gregory et al. | 606/8 |
| 6,096,018 A | 8/2000 | Luzio et al. | 604/500 |
| 6,126,645 A | 10/2000 | Thompson | 604/245 |
| 6,258,118 B1 * | 7/2001 | Baum et al. | 623/1.19 |
| 2002/0082610 A1 * | 6/2002 | Cioanta et al. | 606/108 |

FOREIGN PATENT DOCUMENTS

| | | |
|---|---|---|
| EP | 0604022 | 6/1994 |
| EP | 0652017 | 5/1995 |
| WO | WO 93/06792 | 4/1993 |
| WO | WO 00/21584 | 4/2000 |

\* cited by examiner

Primary Examiner—David H. Willse
Assistant Examiner—Javier S. Blanco
(74) Attorney, Agent, or Firm—Christie, Parker & Hale, LLP

(57) ABSTRACT

An expandable stent for use within a body lumen that is coated with a radiation-absorbing material and that is not plastically expandable at normal body temperatures but is expandable at a temperature between about 38° C. to 60° C. following exposure to radiation. The invention also relates to a method of deploying such a stent within the body.

42 Claims, 6 Drawing Sheets

METHOD FOR DEPLOYING A THERMO-MECHANICALLY EXPANDABLE STENT

FIELD OF THE INVENTION

The present invention relates generally to medical devices and methods for deploying the same, and more particularly, to stents coated with a radiation-absorbing material and methods for inserting and expanding such stents within a lumen of the body.

BACKGROUND OF THE INVENTION

Stents, including cardiovascular and biliary stents, are well known as devices that are used to support a body lumen, such as an artery, vein, biliary duct, or esophagus. They may be employed as a primary treatment for a constriction of a body lumen (stenosis), or may be used following a medical procedure, such as angioplasty, used to remedy stenosis. Percutaneous transluminal coronary angioplasty is one of the primary methods used to treat coronary artery disease. Percutaneous transluminal angioplasty of peripheral and visceral vessels as well as of other body lumens is also used to treat diseases known to be associated with those anatomical regions.

Conventional stents have taken two forms, each having a deployment method that is peculiar to the construction of the stent. First, there are self-expanding stents that typically are made of metal, and that may include a biocompatible coating. Generally, such stents are permanently implanted into the human body by deploying them on or through a catheter. The stent is placed in tension or compression at the distal end of the catheter, and percutaneously inserted into the body where it is guided to the site of implantation. The stent then is released from the distal end of the catheter, where it expands to a fixed, predetermined diameter, and is held in position as a result of that expansion and inward pressures exerted by the lumen.

A proposed variation on a self-expanding stent uses a material, such as nitinol, having a "shape memory." A stent constructed from such material would be designed in a fully expanded configuration, then compressed into a second configuration so that it may deployed on a catheter to be inserted into the body percutaneously, and heated either before or after insertion into the body to return to its fully expanded configuration when released from the catheter. Alternatively, the compressed stent is chilled below body temperature, returning to its fully expanded state after the stent temperature has passively risen to body temperature following insertion into the body.

A second type of stent commonly used in the field is expandable as a result of mechanical action by the operator. One such stent is disclosed in Palmaz, U.S. Pat. Nos. 4,733,665, 4,776,337 and 4,739,762. According to the Palmaz patents, an unexpanded stent is permanently implanted in the body by percutaneously inserting it into a vessel using a catheter, and guiding the stent to the site where it is to be permanently implanted. Upon reaching the site of permanent implantation, the balloon portion of the catheter is inflated and the stent expanded, solely as a result of the mechanical force applied by the expanding balloon, until the stent is sized appropriately for the implantation site. Thereafter, the expanded balloon is deflated, and the catheter is removed from the body, leaving the stent permanently in position.

The use of thermo-mechanical techniques for forming polymeric structures within a body lumen is disclosed in Pathak et al., U.S. Pat. No. 5,741,323. According to that patent, a light-absorbing compound such as a chromophore is blended within a polymeric device that is intended to be deployed within the body lumen. The shape of this device may be modified in vivo by using a light source to heat the article to a temperature at which the material is flowable.

Because the chromophore is compounded into the polymer at a desired weight percentage, however, there is an increased risk of altering the stent's mechanical properties, and thus its overall performance. Also, the sole purpose of the chromophore in the stent is to cause the stent to be heated for deployment; once this is accomplished, the chromophore is no longer needed in the body. Because the chromophore is compounded with the polymeric article throughout the entire polymer matrix, the chromophore persists in the body as long as the polymeric article remains in place. Thus, the risk of an adverse reaction to the chromophore is increased due to increased residence time and sustained release in the body.

Moreover, by blending the chromophore through the entire polymer matrix, selective heating of portions of the article is impossible, and indeed, because the interior of the article closest to the balloon will be heated first and longest, the method described by Pathak poses the risk that the balloon may be damaged by overheating. In addition, compounding the chromophore with the polymer by thermal means can alter its light-absorbing properties or degrade it significantly. Chromophores which are compounded with polymers and extruded to make stents may become photo-bleached, altering their absorption properties and making precise and repeatable deployment difficult. Chromophores can also chemically react with the polymer during heating, leading to cross-linking which may alter the physical properties of the polymer. Finally, as the polymeric stent expands, any fenestrations in the stent expand as well, creating regions devoid of chromophore and resulting in a drop in the efficiency of heating the stent.

Therefore, recognizing the desirability of expandable stents, it is necessary to provide a mechanism for deploying such stents within the body that overcomes the problems just noted.

SUMMARY OF THE INVENTION

The invention resides in a method for thermo-mechanically deploying a stent in a body lumen. The method comprises first the step of coating the stent with a radiation-absorbing material. The stent is placed at the distal end of a balloon catheter that includes either a radiation source at its distal end or a radiation source that is placed in the catheter lumen. The radiation source is selected to emit radiation that will be absorbed selectively by the radiation-absorbing material. The catheter thus rigged with the stent is inserted into the body lumen, and the stent is heated by generating radiation from the radiation source, which is absorbed by the radiation-absorbing material. Through this process, the radiation is converted to heat and used to warm the stent to a temperature above its glass-transition temperature to thereby become elastic, but below the temperature at which the stent becomes liquid or flowable. At this point, the heated stent is expanded by inflating the balloon catheter to a predetermined size. During expansion, stent temperature is maintained above its glass-transition temperature. Upon reaching that size, radiation is no longer supplied to the stent, which is allowed to cool below its glass transition temperature. The stent is thus no longer pliable, so that when the catheter is deflated, it may be withdrawn from the body leaving the expanded stent within the body lumen, the stent having sufficient hoop strength to support the lumen as desired.

BRIEF DESCRIPTION OF THE DRAWINGS

These and other features, aspects, and advantages of the present invention will be more fully understood when considered with respect to the following detailed description, appended claims, and accompanying drawings, wherein:

DETAILED DESCRIPTION OF THE INVENTION

The invention resides in a method for deploying a thermo-mechanically expandable stent in the body. A stent that may preferably be used in the present invention is that described in Healy et al., U.S. Pat. No. 5,670,161, hereby incorporated by reference in its entirety. Such a stent is preferably comprised of a biodegradable copolymer of L-lactide and ε-caprolactone.

The relative amounts of each of L-lactide and ε-caprolactone in the copolymer are selected to produce thermal and mechanical properties that permit the copolymer to be thermo-mechanically expandable at temperatures in the range of about 38 to about 60 degrees Celsius (°C.) using a balloon catheter, while remaining sufficiently rigid and strong at normal body temperatures to support the body lumen. Copolymers having a molar ratio of L-lactide to ε-caprolactone of about 90:10 to about 98:2 (as determined by conventional NMR analysis) are believed to be useful in the present invention. Other biodegradable materials, including polymers, copolymers, or polymer blends of D,L-lactide, glycolide, L-lactide, ε-caprolactone, and/or poly(ethylene glycol), that exhibit similar thermo-mechanical properties also may be used in the present invention without departing therefrom.

Figure 1:
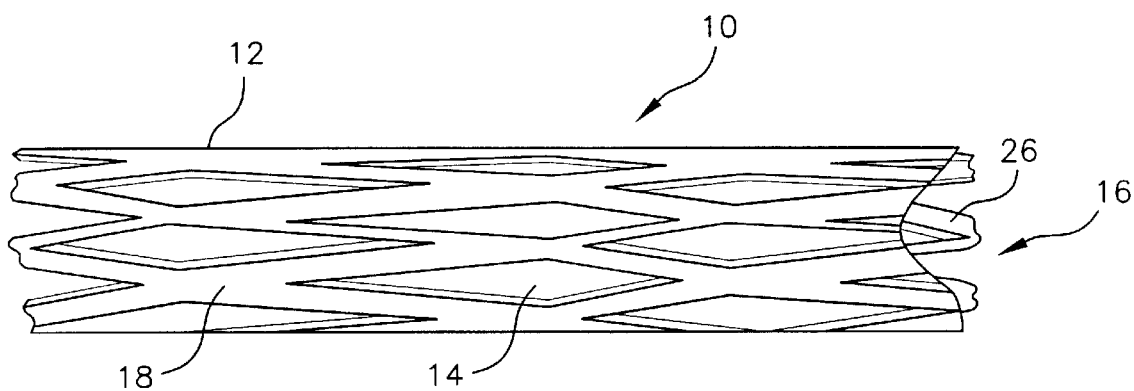
FIG. 1 is a semischematic drawing of an embodiment of an unexpanded stent according to practice of the present invention.

The stent of the present invention comprises a cylindrical tube of appropriate size to be inserted into a body lumen, and thus typically is about 1 cm to about 10 cm in length, about 1 mm to about 3 mm in unexpanded diameter and about 3 mm to about 12 mm in expanded diameter. For clinical applications, the stent is most frequently 1 cm to 3 cm in length and 1 mm to 4 mm in unexpanded diameter, 3 mm to 8 mm in expanded diameter. Turning to FIG. 1, there is shown a stent 10 useful in accordance with practice of the present invention. In FIG. 1, the stent is shown in its unexpanded state. The stent comprises a hollow cylindrical tube 12 and may contain perforations 14. Alternatively, the stent may be imperforate.

Perforations in the walls of a stent reduce the amount of material that must be heated to permanently deploy the stent using thermo-mechanical means. As a result, stents with perforations require a lessor amount of heat for deployment than those without perforations. Perforations also allow in-growth of endothelial cells into the interior 16 of the stent. Such cell in-growth may result in more complete or faster endothelial coverage of the stent and may be desirable where, for example, the stent may become a site for thrombosis, or clotting, to occur.

In order to practice the method of the present invention, the stent first is prepared by coating the stent with a radiation-absorbing material that will heat upon exposure to a particular radiation. A preferable radiation-absorbing material is indocyanine green, which is known to be tolerated within the body in low concentrations for short times. However, any other radiation-absorbing material compatible and safe for use within the body, for example, methylene blue, vital blue or other dyes currently approved for use in biodegradable sutures. Carbon black may also be used, although carbon black is particulate and may attract macrophage to the site of stent deployment. Preferably, the radiation-absorbing material is combined in solution with a biodegradable coating material for fixing the radiation-absorbing material to the stent. Alternatively, the radiation-absorbing material is applied directly to the stent without a coating material.

The coating material may be composed of the same material as the stent, preferably at lower molecular weights than is found in the stent material. Preferably, the coating material degrades more quickly than the polymeric material from which the stent is prepared. For the stent described in Healy et al., U.S. Pat. No. 5,670,161, the coating material preferably includes D,L-lactide, a copolymer of D,L-lactide and glycolide, or a copolymer of L-lactide and ε-caprolactone (with lower molecular weights of each of these copolymers than found in the stent itself). However, any biodegradable coating material comprised of a polymer, copolymer, or polymer blend containing one or more compounds selected from the group consisting of D,L-lactide, glycolide, L-lactide, and ε-caprolactone, may be used.

Preferably, the coating material also includes a lubricious material that reduces the risk of thrombosis. Suitable lubricious materials include poly(ethylene glycol), poly(vinyl alcohol), poly(vinyl pyrrolidone), poly(acrylic acid), poly(methacrylic acid) and polyacrylamide. Monomers of those materials also may be employed, as may fats, gums, and other materials having similar lubricious effects. In addition, phospholipids, such as phosphorylcholine and/or phosphatidylcholine, and polymerized phospholipid analogues, such as 2-methacryloyloxyethyl phosphorylcholine (MPC), can be used exclusively or as a blend in the coating material.

The coating material also may include drugs or other molecules and components to be delivered to the site where the stent is deployed. Such drugs may include antithrombotics (such as anticoagulants), antimitogens, antimitotoxins, antisense oligonucleotides, gene therapy vehicles, nitric oxide, and growth factors and inhibitors. Direct thrombin inhibitors believed to be useful in the invention include hirudin, hirugen, HIRULOG (Biogen, Inc.), PPACK (D-phenylalanyl-L-propyl-L-arginine chloromethyl ketone), argatreban and D-FPRCH$_2$Cl (D-phenylalanyl-L-propyl-L-arginyl chloromethyl ketone). Indirect thrombin inhibitors include heparin and warfarin. Materials capable of β-particle emission also may be useful to inhibit neointima formation. These materials preferably are incorporated in quantities that permit desirable timed release as the coating material degrades.

Additionally, the coating material may also include a photo-activated drug such as hematoporphyrin derivative (HpD), 5-aminolevulinic acid (ALA), a phthalocyanine, chlorin, purpurin, bensoporphyrin, or texaphyrin. Such a photo-activated drug is useful, for example, in the treatment of atherosclerotic plaques. By incorporating the photo-activated drug into the coating material of a stent, the drug is selectively placed at the atherosclerotic plaque site during stent deployment at a concentration greater than could be achieved by systemic loading of the drug. In one embodiment, the drug is activated during stent deployment by the same radiation that heats the stent. Alternatively, the drug is activated subsequent to stent deployment by a different radiation source. The photo-activated drug could thus be used to modulate the tissue response at the atherosclerotic plaque site.

As discussed above, the coating material is preferably combined in solution with the radiation-absorbing material prior to coating the stent. In another embodiment, the radiation-absorbing material is applied directly to the stent and the coating material is applied over the radiation-absorbing material. In still another embodiment, the radiation-absorbing material and the coating material are applied as a multilayer laminate. In this embodiment, the coating material is applied to the stent before and after the application of the radiation-absorbing material, forming a laminate containing a first layer of coating material, a second layer of radiation-absorbing material, and a third layer of coating material.

Any suitable technique for coating the stent may be used, including preferably spray coating, dip coating, or any other technique that can provide a well-controlled, uniform coating thickness and density to ensure that sufficient radiation-absorbing material is applied to and retained upon the stent. Thus, a radiation-absorbing coating may be formed from an indocyanine green/coating material solution, which is sprayed onto the exterior surface of a stent in a thickness of about 60 to about 110 microns, and preferably from about 70 to about 90 microns. In functional terms, the radiation-absorbing coating should be thick enough to absorb 75 to 100 percent of the radiation transmitted to it as described below. For example, it has been determined that a radiation-absorbing coating formed from a solution containing 75.9 wt. % acetone, 18.9 wt. % methanol, 0.2 wt. % indocyanine green, and 5.0 wt. % RESOMER® (produced and distributed by Boehringer Ingelheim Pharma KG), which may be poly(L-lactide), poly (D,L-lactide), poly (D,L-lactide-co-glycolide) or other suitable absorbable polymers, is useful in the present invention. With reference to FIG. 1, the stent may be fabricated with a coating 18 on its exterior surface or a coating 20 on its interior surface, or it can have coatings on both surfaces. Alternatively, selected portions of the stent may be coated if there are certain areas in which it is desired to provide heating while in other areas no heating is desired. Typically, the stent will be coated prior to sterilization and deployment, and it is not anticipated that the operator will perform the coating step.

Using a coating material containing the same polymeric material as the stent, although at a lower molecular weight, will result in good adhesion of the radiation-absorbing coating to the stent. Over time, the lower molecular weight coating material will degrade more easily than the stent and the radiation-absorbing material in the coating will be removed from the stent sooner. Preferably, the radiation-absorbing material will be excreted or otherwise removed from the body, rather than absorbed into the wall of the vessel lumen. The lower molecular weight coating is also more deformable, expanding as the stent expands without cracking or flaking. When the radiation-absorbing material/coating material is sprayed onto the stent, the resulting coating is more porous than the stent itself.

Figure 2:
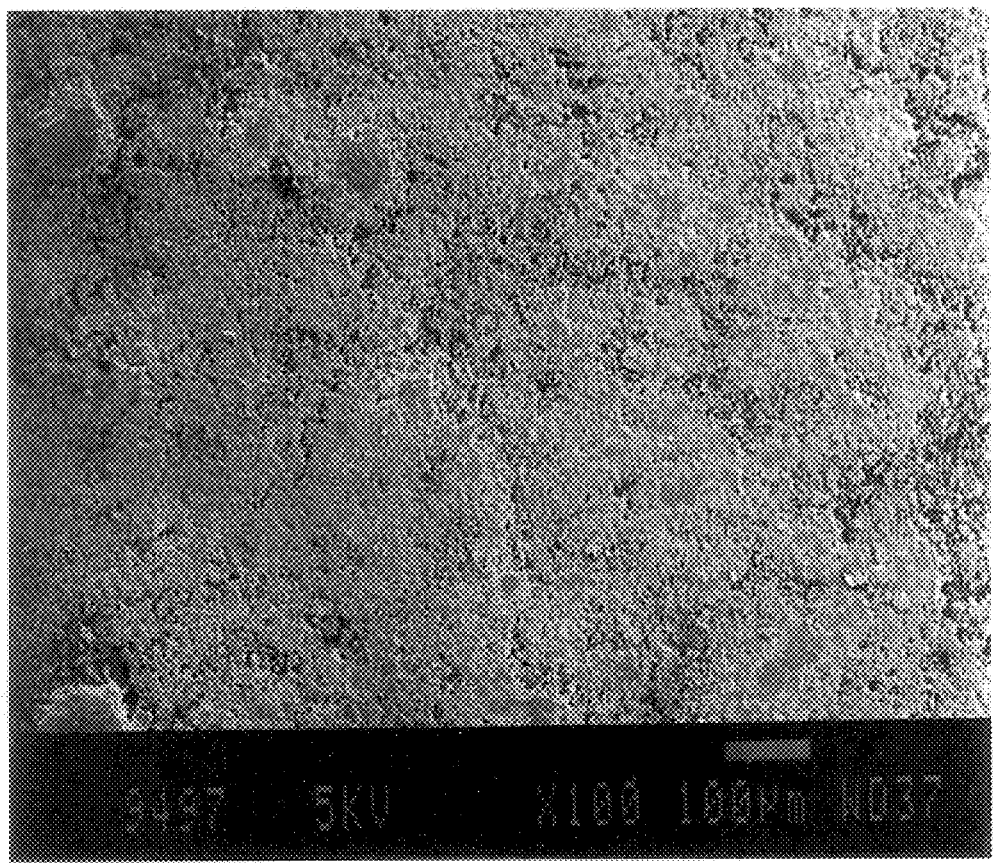
FIG. 2 is a scanning electron micrograph of the surface of a stent that has been spray coated with a radiation-absorbing coating material provided in accordance with practice of the present invention, shown before expansion of the stent.
Figure 3:
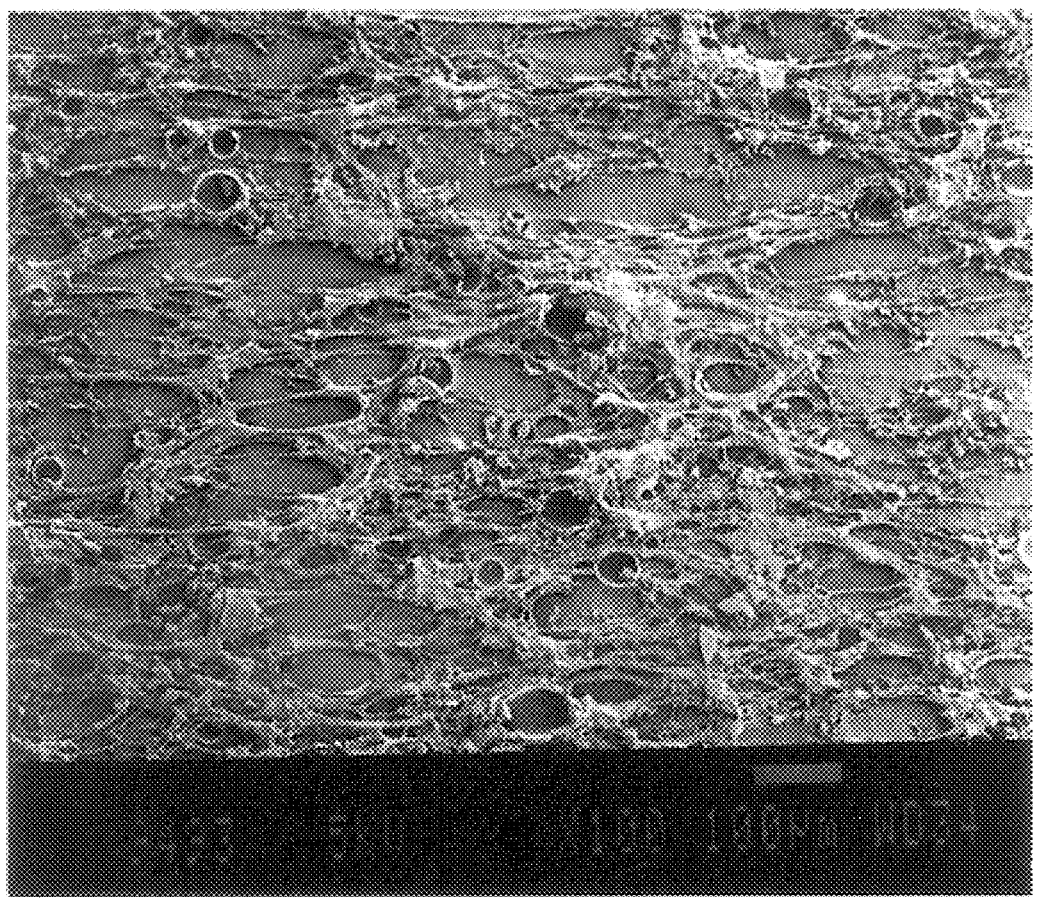
FIG. 3 is a scanning electron micrograph of the surface of the stent of FIG. 2, shown after expansion of the stent.

Turning to FIGS. 2 and 3, there are shown scanning electron micrographs, magnified 100-fold, of the surface of a stent that has been spray coated with a radiation-absorbing coating material provided in accordance with practice of the present invention. FIG. 2 shows the stent before expansion and FIG. 3 shows the stent after expansion. As shown in FIG. 2, the spray coating process deposits a uniform microporous coating over the outer surface of the stent. The deposition parameters allow for good adhesion between the sprayed coating and the underlying polymeric stent.

The coated stent is loaded onto the collapsed balloon of a balloon catheter. At this time, the balloon may be expanded slightly in order to secure the stent, or the stent may be secured within a deployment sheath.

In order to heat the coating of the stent, and thereby heat the stent, it is necessary that radiation, in the preferred embodiment light, be delivered to the coating. Other forms of radiation may be used, including microwaves, ultrasound, and radio waves.

In a preferred embodiment, optical radiation will preferably be delivered to the coating via an optical fiber that runs within the catheter. The radiation is coupled into the optical fiber at the fiber's proximal end and is emitted from an optical diffuser attached to the optical fiber's distal end. The diffuser is located within the balloon portion of the catheter. The diffuser directs the radiation radially outward from the axis of the fiber uniformly along the entire length of the diffuser such that, in the preferred embodiment, the optical irradiance preferably is approximately uniform along the length of the stent.

At the proximal end, the optical fiber is connected to a provider of radiation, in the preferred embodiment a laser, that emits radiation within a wavelength range that is absorbed by the coating on the stent. The absorbed radiation is converted to heat, raising the temperature of the stent above its glass transition temperature and thereby making the stent easily deformable. The wavelength range should be selected so that the radiation is not absorbed significantly by, and is readily transmitted through, the wall of the balloon on the catheter. Where the radiation-absorbing material is indocyanine green, it is preferred that the wavelength of light employed is about 770 nm to about 830 nm. Where the radiation-absorbing material is methylene blue, it is preferred that the wavelength of light employed is about 580 to about 700 nm. Where the radiation-absorbing material is carbon black, which absorbs strongly from the ultraviolet to the infrared, the wavelength of light can vary from the ultraviolet to the infrared (about 350 nm to about 1100 nm).

The optical power emitted from the diffuser and transformed into heat in the coating of the stent needs to be controlled. To control the power emitted from the diffuser, one can control the power coupled into the proximal end of the optical fiber by controlling power emitted by the radiation provider. Other methods of controlling the power emitted from the diffuser are known to those skilled in the art. As more power enters the optical fiber, more power is emitted from the diffuser, more power is absorbed by the coating, and the temperature of both the coating and the stent rises. In this invention, it is necessary to control the power emitted from the diffuser to avoid heating the stent to too high a temperature, which could cause bodily injury and/or result in damage to the stent or balloon, while at the same time heating the stent above its glass transition temperature to permit the stent to become pliable and to be expanded. Also, if the optical power is not controlled, the radiation-absorbing material in the coating or contrast medium may become photobleached, reducing the efficacy of the radiation-absorbing material in maintaining the temperature of the stent.

According to the method of practice of the present invention, the coated stent and catheter, as described above, are inserted percutaneously into a body lumen and guided to the area of deployment using conventional techniques well known to the field. The radiation provider is turned on and radiation emitted from the diffuser impinges upon the stent coating, thereby heating the stent.

In one embodiment of the method of deploying the stent, a guide wire is directed to the site of deployment. The stent and the balloon catheter to which it is secured are positioned over the guide wire and directed to the site of deployment; the guide wire is then removed. A pre-measured length of optical fiber, with a diffuser attached at its distal end and a locking device attached along its length, is selected such that the distance from the diffuser to the locking device is equal to the distance from the catheter balloon to a catheter hub located outside the body of the patient. The pre-measured optical fiber is passed through the catheter lumen to thereby automatically position the diffuser within the balloon portion of the catheter, securing the locking device on the optical fiber to the hub of the catheter.

Figure 4:
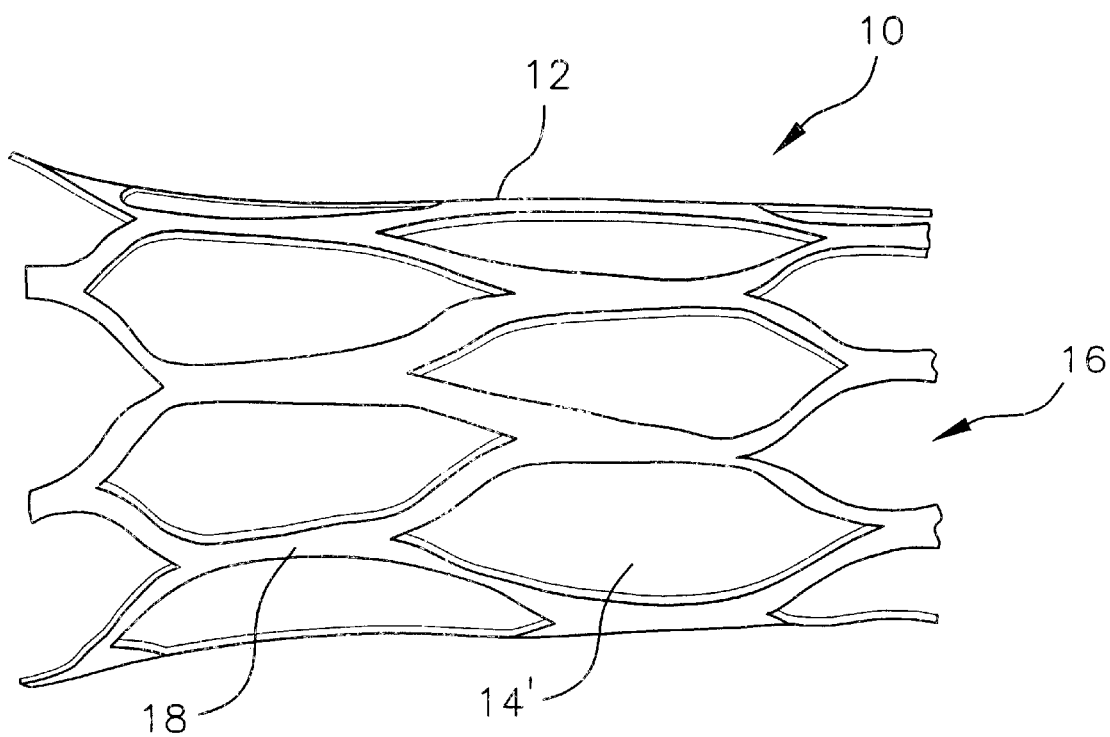
FIG. 4 is a semischematic drawing of the end portion of the stent of FIG. 1 after expansion.

After the stent has been properly heated, as discussed below, a contrast medium is injected into the balloon portion of the catheter thereby expanding the balloon and thus the stent. Turning to FIG. 4, there is shown an end of the stent of FIG. 1 in its expanded state. The perforations in the stent expand as the stent expands thereby forming enlarged perforations or fenestrations 14' in the cylindrical tube 12 of the stent 10.

The contrast medium is any conventional medium, but to aid the heating of the stent it is preferable that the medium contains a material that will absorb the radiation emitted from the diffuser. That radiation-absorbing material may be the same absorbing material that is used in the coating, or may be a different material. The purpose of including a radiation-absorbing material in the contrast medium is to minimize the fraction of radiation that escapes through fenestrations in the stent that develop as the stent expands. Also, by including a radiation-absorbing material in the contrast medium, less radiation-absorbing material is needed in the stent coating. If the concentration of radiation-absorbing material in the stent coating is sufficiently high to heat the fenestrated stent in its expanded state in the absence of radiation-absorbing material in the contrast medium, the stent may become overheated when exposed to radiation in the unexpanded state, causing damage to the stent, balloon and surrounding tissue. The radiation-absorbing material also may become photo-bleached, and thereafter less effective in heating the stent.

For stents that develop fenestrations during expansion, the concentration of radiation-absorbing material in the contrast medium is set to limit the total fraction of radiation that propagates beyond the stent and into the adjacent tissue. Conversely, the optical density of the contrast medium should be such that a fraction of the radiation is transmitted through the contrast medium and is absorbed directly by the stent coating, thus limiting the direct heating of the contrast medium and allowing continued direct heating of the stent.

The concentration of radiation-absorbing material used in the contrast medium may be determined empirically. In one embodiment of the invention, indocyanine green ("ICG") is used in both the coating and in the contrast medium, in a concentration of 48.1 mg ICG/g poly(D,L-lactide) in the coating, and between about 0.15 and about 0.4 mg/mL, preferably 0.2 mg/mL, in the contrast medium. If the concentration of indocyanine green in the contrast medium is too high, about 0.5 mg/mL or higher, insufficient radiation penetrates the medium and only the contrast medium near the diffuser lumen is heated. Under these circumstances, the medium near the diffuser may become overheated and damage the diffuser. Conversely, if the concentration of indocyanine green used in the contrast medium is too low, about 0.1 mg/mL or lower, the contrast medium may not be sufficiently heated by the radiation emitted from the diffuser to maintain a stable temperature. Suitable concentration ranges of other radiation-absorbing materials may be determined empirically or by methods known by those skilled in the art, with consideration given to factors such as the extinction coefficient and attenuation properties of the material.

Before the balloon is inflated with contrast medium, almost all of the increase in stent temperature results from the absorption of radiation by the stent coating. As contrast medium enters the balloon, causing the balloon (and the stent) to expand, some of the radiation is absorbed by the contrast medium, raising the temperature of the medium. By employing the radiation-absorbing material in the contrast medium as well as in a coating, it is possible to heat the stent (and thereby to soften it) more efficiently than using the radiation-absorbing material only in the coating.

The heat generated using the radiation source will raise the temperature of the stent sufficiently above its glass transition temperature to render the stent pliable, and therefore to expand upon application of mechanical force (thermo-mechanical expansion). The amount of time needed to reach this temperature will vary depending upon the radiation-absorbing material, its concentration and use as either or both a coating applied to the stent and within the contrast medium, and the heat capacity of the stent, as well as the power emitted from the diffuser. The rate at which the temperature of the stent rises within the body upon heating using the light source also may vary from body lumen to body lumen, depending upon the rate of blood or other fluid flow through the lumen and the thermal properties of the adjacent tissue. Thus, to ensure sufficient heating and safe deployment within the body, it will be necessary either to determine the heating time and power empirically or to use a feedback system to control the power delivered to the coating and thus control the stent temperature. Experimentation may yield the empiric heating time and power necessary to soften the stent adequately for expansion. In the preferred embodiment, however, a feedback system is used to modulate the power and control the stent temperature. A thermocouple is placed between the balloon and the stent to provide a continuous measure of the stent temperature; those skilled in the art could use another of several temperature sensing devices to provide the necessary thermal feedback signal for control of the stent temperature. The temperature sensed by the thermocouple is fed into a controller system, preferably a proportional-integral-differential controller system, that modulates the power emitted from the diffuser, preferably by modulating the power emitted from the radiation provider, thereby maintaining the stent temperature to within a range above the glass transition temperature that permits stent expansion yet does not adversely overheat the tissue adjacent to the stent, preferably the stent temperature is maintained between about 38° C. and about 60° C. depending upon the molecular composition of the stent.

Once the stent has been heated sufficiently to permit expansion, a controlled volume of the contrast medium is injected into the balloon to expand the balloon, and thereby to expand the stent as a result of the mechanical force applied by the balloon. The balloon is expanded using conventional techniques of injecting contrast medium into the balloon at a controlled rate so as to avoid bursting the balloon and/or damaging the body lumen, and so as to avoid rapid fluctuations in the temperature of the stent.

Because the stent has been made pliable as a result of heating, it does not offer substantial resistance to the expansion of the balloon. Thus, the expansion of the balloon to its nominal, fully expanded diameter is to be facilitated by the pressure of the contrast medium within the balloon in accordance with conventional techniques. During balloon expansion, it may be necessary to modulate the power emitted from the diffuser in order to maintain the stent within the proper temperature range. Although it may be possible to modulate the power empirically, in the preferred embodiment the feedback controller modulates the power based upon the temperature sensed by the thermocouple placed between the balloon and the stent.

Upon expansion of the stent, the adhesion between the coating and the stent is remarkably strong. As shown in the scanning electron micrograph of FIG. 3, the plastically deformed coating expands with the underlying stent without either spalling or cracking off the stent surface. The expanded coating has increased texture and surface area compared to the coating as deposited, which is beneficial for maintaining the stent position after placement within the body lumen. In addition, the textured coating provides a good surface for cellular integration with the stent.

After the balloon is fully expanded, the radiation source is turned off, and the heat used to soften the stent is permitted to dissipate within the body. This cools the stent below its glass transition temperature to the point where it is no longer pliable, and the stent therefore remains in its expanded state. Following this period of heat dissipation, the contrast medium is removed from the balloon using conventional techniques, and the collapsed balloon and catheter are removed from the body, leaving the stent behind in its place in the body lumen.

In the embodiment described above, optical radiation is provided to the stent coating via a diffuser contained within the lumen of the balloon on which the stent is deployed. In this embodiment, the internal diffuser is connected to an external laser, which provides optical radiation to the diffuser via optical fibers. It is contemplated that in other embodiments, the radiation source will be contained in a single device as, for example, in an ultrasonic transducer. In such embodiments, the radiation source may be completely contained within the balloon and not dependent on an external component. It is to be understood that both embodiments, that is, those in which the radiation source includes an internal and an external component, and those in which the radiation source is contained in a single internal component, are provided in accordance with practice of the present invention.

Examples of the deployment method of the present invention are set forth below.

EXAMPLE 1

Manual Control of Laser Power

A stent provided in accordance with the present invention, 2 cm in length and composed of a copolymer of L-lactide and ε-caprolactone with a nominal molar ratio of L-lactide to ε-caprolactone of 93:7, was spray coated on its exterior surface with a 81.8 μm coating of indocyanine green and RESOMER® RG503 poly(D,L-lactide-co-glycolide) (i.v.= 0.4) in 80/20 v/v acetone/methanol solution; no interior coating was applied. The coating solution contained 75.9 wt. % acetone, 18.9 wt. % methanol, 0.2 wt. % indocyanine green, and 5 wt. % RESOMER® RG503 poly (D,L-lactide-co-glycolide). The stent was placed upon a Schneider Total Cross 0.021-inch balloon (6 mm diameter, 2 cm length; Schneider (USA), Inc.) with a thermocouple between the balloon and the stent. A 3 cm long, 0.019-inch diameter, optical diffuser (Lightstik®, Rare Earth Medical, Inc.) was inserted into the lumen of the balloon, and an optical fiber connected the diffuser to the continuous wave output of a diode laser emitting 790.7 nm radiation (Opto Power Corp., model OPC-D010-B05-HPHS/250, maximum output power at 10 W).

A small amount of contrast medium containing a concentration of 0.2 mg/mL of indocyanine green was injected into the balloon at a pressure of 1 atm. The catheter and stent were inserted percutaneously into a blood vessel of a pig, and located using conventional fluoroscopy to the site where the stent was to be deployed. Once in the vessel, the diode laser power was turned on, the output from the diode laser was increased, and the temperature of the stent was brought to about 55° C. for 2 minutes. After 2 minutes, and while the stent temperature was maintained above about 50° C., the balloon was expanded by increasing the pressure inside the balloon from the initial pressure of 1 atm to about 8 atm in about 2 minutes. During stent expansion, the laser current was manually adjusted to maintain a stent temperature greater than 50° C. The laser power was then turned off.

Figure 5:
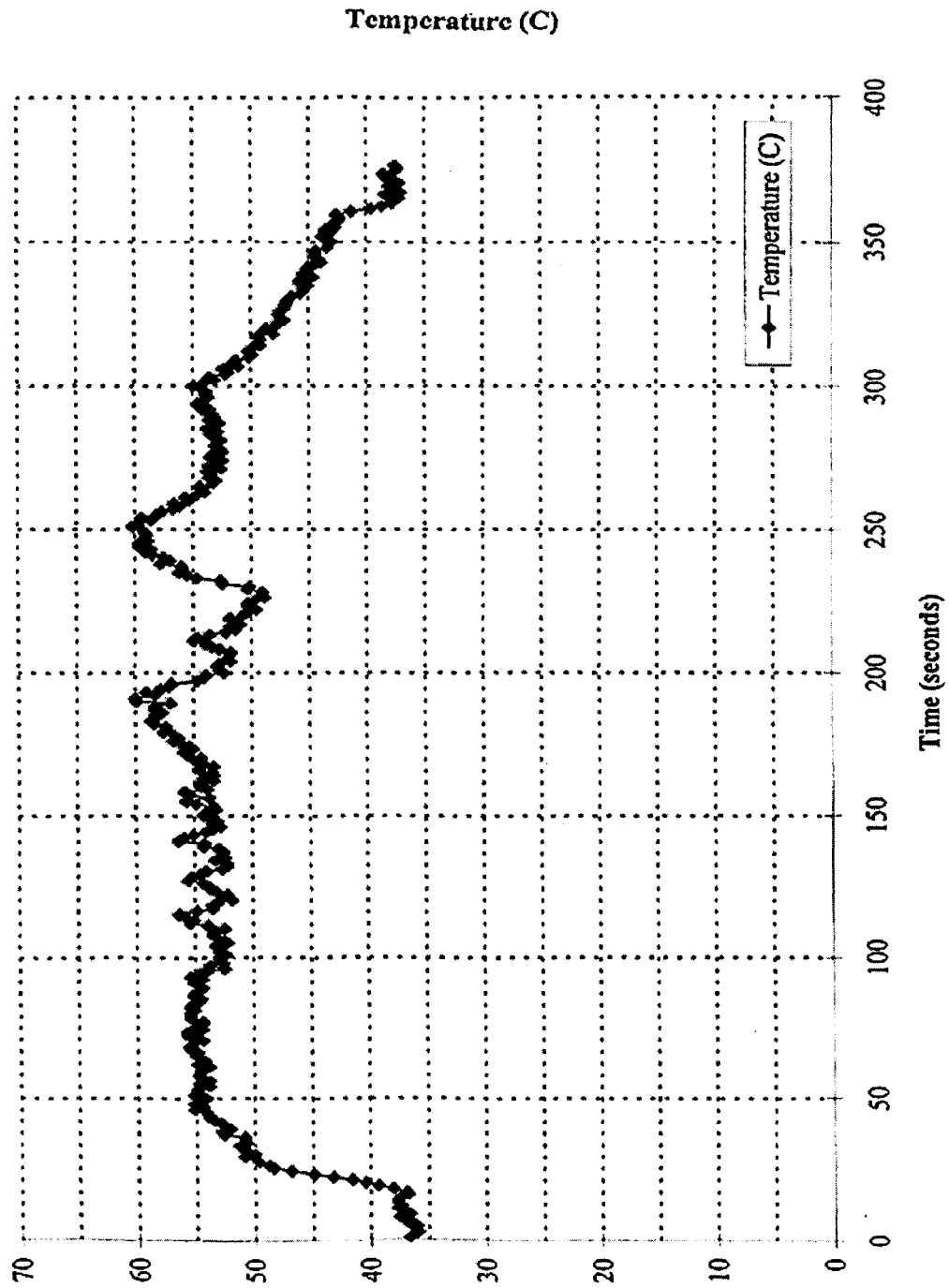
FIG. 5 is a graph showing the relationship between the temperature of the stent and the time of exposure to optical radiation in accordance with practice of the present invention.

The stent passively cooled to about 42° C., at which time the stent was no longer pliable. The balloon was then collapsed and the catheter withdrawn. Immediate post-mortem inspection of the vessel revealed a fully expanded stent with hoop-strength sufficient to slightly distend the vessel lumen by about 110% of its initial diameter. Turn now to FIG. 5, which shows the change in temperature of the stent as a function of time for this example.

In this example, the temperature of the stent was controlled by manually adjusting the output power of the diode laser. However, the temperature of the stent can be controlled automatically by employing a thermocouple and interfacing the laser with a microcomputer with an automated temperature-control algorithm, thereby modulating the power delivered to the stent to control the stent temperature and thus providing improved temperature control.

EXAMPLE 2

Automatic Control of Laser Power

A stent of 2 cm in length, having the same composition as the stent of Example 1, was spray coated on its exterior surface with a 120.7 μm coating of indocyanine green and RESOMER® R202 poly(D,L-lactide) (i.v.=0.2) in 80/20 v/v acetone/methanol solution; no interior coating was applied. The coating solution contained 75.9 wt. % acetone, 18.9 wt. % methanol, 0.2 wt. % indocyanine green, and 5 wt. % RESOMER® R202 poly(D,L-lactide) (i.v.=0.2). The stent was placed upon a Schneider Total Cross 0.021-inch balloon (6 mm diameter, 2 cm length; Schneider (USA), Inc.) with a thermocouple between the balloon and the stent, with a 3 cm long, 0.019 inch diameter, optical diffuser (Lightstik®, Rare Earth Medical, Inc.) within the lumen of the balloon and an optical fiber connecting the diffuser to the output of a continuous wave diode laser emitting 811.1 nm radiation (Opto Power Corp., model OPC-D010-B05-HPHS/250, maximum output power at 10 W). In this example, the laser was interfaced with a microcomputer with an automated temperature control algorithm.

A small amount of contrast medium containing a concentration of 0.2 mg/mL of indocyanine green was injected into the balloon at a pressure of 1 atm. The catheter and stent were inserted percutaneously into a blood vessel of a pig, and located using conventional fluoroscopy to the site where the stent was to be deployed.

Figure 6:
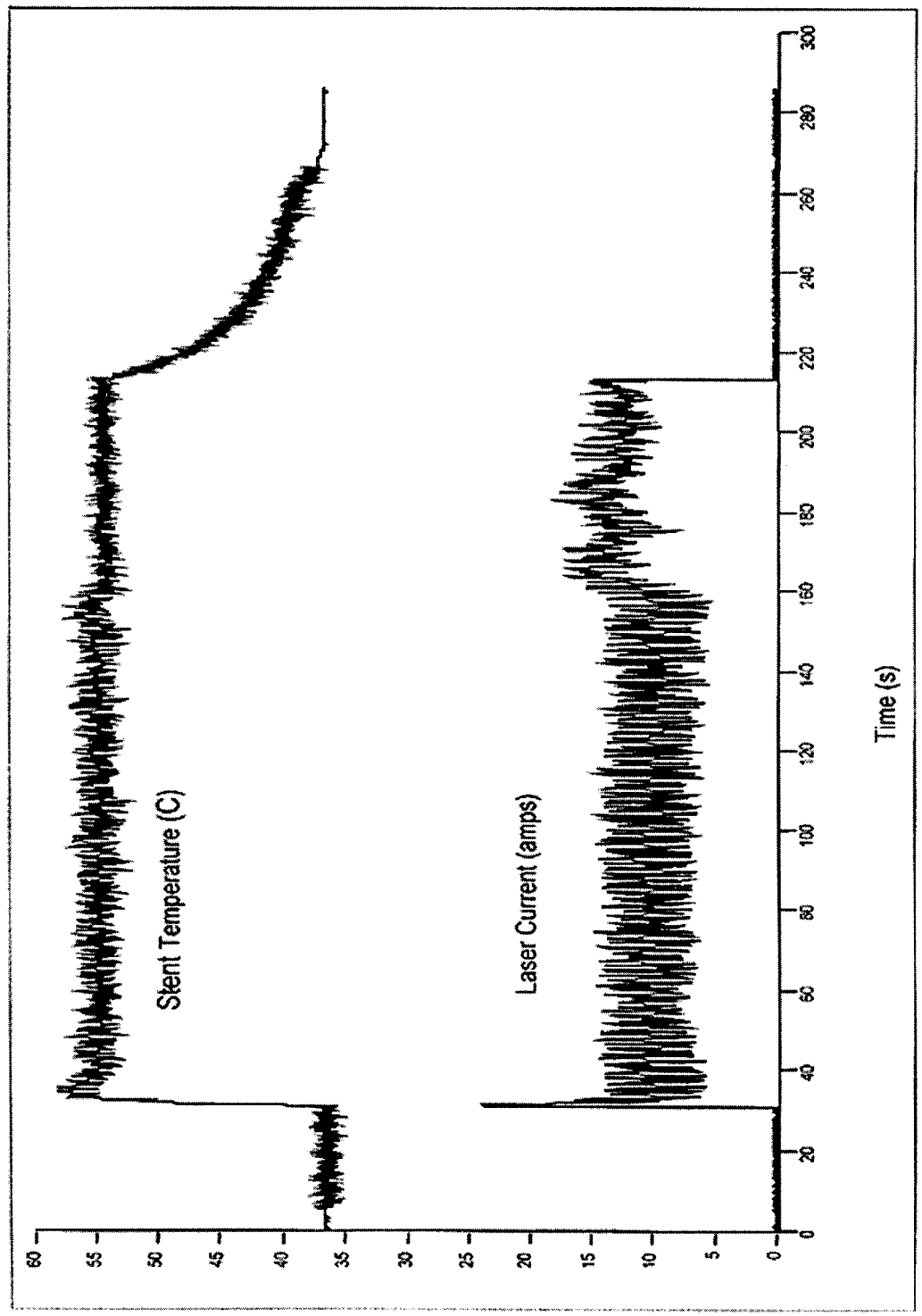
FIG. 6 is a graph showing the relationship between the temperature of the stent, the current of the laser providing optical radiation, and the time of exposure to optical radiation in accordance with practice of the present invention.

Turning now to FIG. 6, there is shown the stent temperature, in °C., and laser performance, in amps, as a function of time during the heating and deployment of the stent in the left internal iliac of a pig. The temperature at the balloon stent interface was sensed by a thermistor. The current to the diode laser was automatically adjusted to maintain a temperature of about 55° C. The actual current supplied to the laser diode was sensed and recorded. As shown in FIG. 6, immediately after the laser was turned on (at thirty seconds), the stent temperature increased to about 55° C. and remained at 55° C. for about 2 minutes. Stent expansion began at about 160 seconds, 130 seconds after the laser was turned on, at which time pressure in the balloon was increased manually by infusion of 0.2 mg/mL indocyanine green mixed with radio-opaque contrast agent. The balloon pressure increased from the initial pressure of 1 atm to about 8 atm in about 40 seconds. Stent temperature was maintained between about 52° C. and about 55° C. during the expansion. The laser was turned off after approximately 210 seconds; the stent cooled passively and returned to body temperature within about 50 seconds. At that time the stent was no longer pliable.

The balloon was then collapsed and the catheter withdrawn. Immediate post-mortem inspection of the vessel revealed a fully expanded stent with hoop-strength sufficient to slightly distend the vessel lumen by about 110% of its initial diameter.

The above descriptions of exemplary embodiments of biodegradable stents and methods for deploying same are illustrative of the present invention. Because of the variations, which will be apparent to those skilled in the art, however, the present invention is not intended to be limited to the particular embodiments described above. The scope of the invention is defined in the following claims.

What is claimed is:

1. A method for deploying a stent in a body lumen, the method comprising the steps of:
   coating the stent with a radiation-absorbing material;
   introducing the stent into a lumen of the body;
   applying radiation from a radiation source to the radiation-absorbing material to thereby heat the stent to at least its glass transition temperature;
   while the stent is at a temperature at or above its glass transition temperature, expanding the stent to a predetermined size; and
   discontinuing application of radiation to the radiation-absorbing material and allowing the stent to cool to a temperature below its glass transition temperature.

2. The method of claim 1, further comprising the step of forming the stent from a material that is degradable within the body lumen.

3. The method of claim 1, further comprising the step of introducing a balloon catheter into the stent and inflating the balloon to thereby expand the stent.

4. The method of claim 3, further comprising the step of introducing a contrast medium into the balloon to thereby inflate the balloon.

5. The method of claim 4, further comprising the step of adding the radiation-absorbing material to the contrast medium, to thereby absorb the radiation and heat the contrast medium.

6. The method of claim 5, wherein the radiation-absorbing material is added to the contrast medium in an amount sufficient to maintain the temperature of the stent at or above its glass transition temperature while absorbing excess radiation to thereby prevent damage to tissue surrounding the stent.

7. The method of claim 1, wherein the radiation source comprises a laser.

8. The method of claim 1, wherein the radiation-absorbing material comprises a chromophore.

9. The method of claim 8, wherein the chromophore is selected from the group consisting of indocyanine green, vital blue, carbon black and methylene blue.

10. The method of claim 1, further comprising the step of blending the radiation-absorbing material with a coating material prior to coating the stent.

11. The method of claim 10, wherein the coating material comprises a polymer, copolymer, or polymer blend containing one or more compounds selected from the group consisting of D,L-lactide, glycolide, L-lactide, and ε-caprolactone.

12. The method of claim 11, wherein the coating material further comprises a lubricious material.

13. The method of claim 12, wherein the lubricious material is selected from the group consisting of poly (ethylene glycol), acrylated poly(ethylene glycol), poly (vinyl alcohol), poly(vinyl pyrrolidone), poly(acrylic acid), poly(methacrylic acid) and polyacrylamide.

14. The method of claim 1, further comprising the step of applying a multilayer laminate to the stent, the multilayer laminate comprising at least one layer of radiation-absorbing material and at least one layer of a coating material.

15. The method of claim 14, wherein the coating material comprises a polymer, copolymer, or polymer blend containing one or more compounds selected from the group consisting of D,L-lactide, glycolide, L-lactide, ε-caprolactone.

16. The method of claim 15, wherein the coating material further comprises a lubricious material.

17. The method of claim 16, wherein the lubricious material is selected from the group consisting of poly (ethylene glycol), acrylated poly(ethylene glycol), poly (vinyl alcohol), poly(vinyl pyrrolidone), poly(acrylic acid), poly(methacrylic acid) and polyacrylamide.

18. A method for thermomechanically deploying a stent in a body lumen comprising the steps of:
   coating the stent with a radiation-absorbing material;
   providing a balloon catheter, the catheter including a radiation source at a distal end, the radiation source selected to emit radiation that will be absorbed selectively by the radiation-absorbing material;
   placing the stent at the distal end of catheter;
   inserting the catheter and the stent into the body lumen;
   heating the stent by generating radiation from the radiation source to be absorbed by the radiation-absorbing material and converted to heat, until the stent exceeds its glass transition temperature;
   inflating the balloon catheter to a predetermined size, thereby expanding the stent to a predetermined size;
   terminating the generation of radiation from the radiation source and allowing the stent to cool below its glass transition temperature;

deflating the balloon catheter and withdrawing it from the body lumen, leaving the expanded stent within the body lumen.

19. The method of claim 18, further comprising the step of selecting a stent that is degradable within the body lumen.

20. The method of claim 18, further comprising the step of selecting a radiation source comprising a laser and a diffuser, the diffuser being positioned along the longitudinal axis of the catheter at the distal end of the catheter and the laser being coupled to the diffuser through an optical fiber, the optical fiber being positioned within the catheter.

21. The method of claim 18, wherein the catheter and stent are inserted into the body percutaneously.

22. The method of claim 18, wherein the radiation-absorbing material comprises a chromophore selected from the group consisting of indocyanine green, vital blue, carbon black and methylene blue.

23. The method of claim 22, wherein the radiation-absorbing material comprises indocyanine green.

24. The method of claim 18, further comprising the step of blending the radiation-absorbing material with a coating material prior to coating the stent.

25. The method of claim 24, wherein the coating material is composed of the same polymeric material as the stent, said coating material having a lower molecular weight than the polymeric material of the stent.

26. The method of claim 24, wherein the coating material comprises a polymer, copolymer, or polymer blend containing one or more compounds selected from the group consisting of D,L-lactide, glycolide, L-lactide, ε-caprolactone, and poly(ethylene glycol).

27. The method of claim 24, wherein the coating material further comprises a drug.

28. The method of claim 27, wherein the drug is selected from the group consisting of antithrombotics, anticoagulants, antimitogens, antimitotoxins, antisense oligonucleotides, gene therapy vehicles, nitric oxide, photoactivated agents, growth factors and inhibitors, hirudin, hirugen, HIRULOG, PPACK, D-FPRCH$_2$CL, peptide-based inhibitors, heparin and warfarin.

29. The method of claim 24, wherein the radiation-absorbing material/coating material is applied to the stent to a thickness of about 40 micrometers to about 200 micrometers.

30. The method of claim 29, wherein the radiation-absorbing material/coating material is applied to the stent to a thickness of about 60 micrometers to about 110 micrometers.

31. The method of claim 18, further comprising the step of selecting a radiation source that emits optical radiation.

32. The method of claim 18, further comprising the step of selecting a radiation source that emits radiation at a wavelength from about 350 nanometers to about 1100 nanometers.

33. The method of claim 18, wherein the radiation source is selected to emit radiation at a wavelength of about 770 nanometers to about 830 nanometers.

34. The method of claim 18, wherein the radiation source is selected to emit radiation at a wavelength of about 580 nanometers to about 700 nanometers.

35. The method of claim 18, wherein the radiation-absorbing material is sprayed on the stent.

36. The method of claim 18, wherein the radiation-absorbing material is applied to the stent in an amount sufficient to absorb between 75% and 100% of the radiation.

37. The method of claim 18, further comprising the step of providing at least one thermocouple to thereby provide a measure of the temperature of the stent.

38. The method of claim 37, further comprising the step of providing a controller that detects the temperature sensed by the thermocouple, said controller modulating the power delivered to the stent to maintain a predetermined temperature of the stent.

39. The method of claim 38, wherein the controller modulates the power delivered to the stent to maintain the temperature of the stent in a range from about 38° C. to about 60° C.

40. The method of claim 18, further comprising the step of selecting a stent that has a glass transition temperature between about 38° C. and about 60° C.

41. The method of claim 18, further comprising the step of introducing a contrast medium into the balloon to thereby inflate the balloon.

42. The method of claim 41, further comprising the step of adding the radiation-absorbing material to the contrast medium.

* * * * *